United States Patent [19]

Klar et al.

[11] Patent Number: 4,504,597

[45] Date of Patent: Mar. 12, 1985

[54] CUPREOUS CATALYST AND PROCESS MAKING SAME

[75] Inventors: Erhard Klar, Beachwood; Don H. Hashiguchi, University Heights; Ronald J. Dietrich, Strongsville, all of Ohio

[73] Assignee: SCM Corporation, New York, N.Y.

[21] Appl. No.: 580,595

[22] Filed: Feb. 16, 1984

Related U.S. Application Data

[63] Continuation-in-part of Ser. No. 548,604, Nov. 4, 1983, abandoned.

[51] Int. Cl.$^3$ .................... B01J 21/04; B01J 23/06; B01J 23/72; B01J 23/74
[52] U.S. Cl. .................... 502/225; 502/226; 502/229; 502/231; 502/244; 502/331; 502/343; 502/345; 502/346; 556/476
[58] Field of Search ............ 502/331, 345, 346, 231, 502/225, 226, 229, 244, 343; 556/476; 241/14

[56] References Cited

U.S. PATENT DOCUMENTS 2,443,902 6/1948 Ferguson et al. ............... 502/345 X
2,889,350 6/1959 Horny et al. .................... 502/346 X

*Primary Examiner*—W. J. Shine
*Attorney, Agent, or Firm*—R. A. Sturges; M. H. Douthitt

[57] ABSTRACT

A grind charge of cupreous particulates containing a major proportion of cuprous and cupric oxides and a minor proportion of elemental copper, said charge having average particle size above 15 microns, is subjected to high energy comminution with concomitant crystal lattice distortion until the average particle size of said particulates is no larger than 15 microns. The resulting catalyst, of fairly high specific surface area, can be used for alkyl or aryl halosilane production.

9 Claims, No Drawings

CUPREOUS CATALYST AND PROCESS MAKING SAME

This is a continuation-in-part application of U.S. application Ser. No. 548,604 which was filed Nov. 4, 1983, now abandoned.

This invention relates to particulate cupreous catalyst and a method for making same, and more particularly to this sort of catalyst for producing an alkyl or aryl halosilane (such as dimethyl dichlorosilane from methyl chloride and silicon) at elevated temperature.

BACKGROUND OF THE INVENTION

A variety of copper/copper oxide catalysts have been made before, including those for alkyl silane production. Usually these are made from precipitated cupreous materials, and these often are contaminated with various impurities such as iron, tin, and siliceous material. The instant invention enables the skilled metallurgist now to make such sort of catalyst more efficiently and with great control of component content.

BROAD STATEMENT OF THE INVENTION

One aspect of the instant invention is a process for producing catalyst from cupreous particles, especially those from pyrometallurgical processing, containing a major proportion of cuprous and cupric oxides and a minor proportion of elemental copper. The process is characterized by: providing a grind charge of said particulates having average particles size above 15 microns, said charge containing zero to about 10% of promoter-providing material; and subjecting said charge to high energy comminution with concomitant crystal lattice distortion until the average particle size of said particulates is no larger than 15 microns.

Another aspect of the instant invention is a pair of cupreous catalysts useful for alkyl or aryl halosilane production. The preferred one is a high cuprous oxide catalyst consisting essentially of about 75–95% cuprous oxide, about 2–10% cupric oxide, about 2–15% elemental copper, and zero to about 10% promoter and having a surface area of about 1–8 square meters per gram, average particle size not substantially above about 15 microns, and exhibiting crystal lattice distortion. The other excellent cupreous catalyst for the same service has a medium content of cuprous oxide. This catalyst consists essentially of about 30–75% cuprous oxide, about 10–45% cupric oxide, about 4–25% elemental copper, and zero to about 10% promoter and has specific surface area of about 2.5–8 square meters per gram, average particle size below 15 microns, and also exhibits crystal lattice distortion.

DETAILED DESCRIPTION OF THE INVENTION

Crystal lattice distortion is evidence of strain energy stored in the catalyst. While not intending to be bound by theory, we believe that, when the catalyst is chemically reduced for chlorosilane manufacture, lattice distortion enhances catalyst activity and utility, e.g., possibly by lowering incubation time to get activity and increasing the surface area of the catalyst. Significant X-ray line broadening when the catalyst is subjected to X-ray diffraction provides evidence of desirable crystal lattice distortion for the instant purpose. The high energy milling (comminution) of the catalyst to at least the very small average particle size called for imparts to the catalyst a significant and useful lattice distortion.

For efficiency and economy the cupreous particulates providing the grind charge (i.e., the charge to the high energy milling operation) generally are no larger than about 80 mesh, advantageously −150 mesh, and preferably preponderantly −325 mesh (so such charge will not unduly restrict production in the high energy milling operation). Average particle size of such grind charge is above 15 microns and ordinarily 90% or more of it will be at least about 25 microns or coarser. Desirably these particulates should not contain more than about a percent of adventitious (that is, normally or inherently present, but not deliberately added) material for best control of charge analysis. The grind charge desirably is extremely low in lead and other impurities that are considered detrimental for silane catalysts. The grind charge can contain, if desired, up to about 10% and usually just a few percent of promoter-providing material such as elemental aluminum, zinc, iron, or the oxides or chlorides of these metals, copper chloride, even a little antimony (below 0.05%), and silica or aluminosilicates typically up to a few percent maximum. The promoter can be an original part of the grind charge of cupreous particulates, or it can be added thereto prior to the high energy comminution the follows. In some instances it can be efficient to add a promoter-providing material such as iron and/or other metal as particles of an alloy of such metal with at least part of the particulate copper that is to be further processed by pyrometallurgy (e.g., oxidation) to make such grind charge for the high energy milling.

Advantageously, for efficiency, economy, and control of product quality, the cupreous material for making the grind charge is mainly directly from (and even more advantageously entirely directly from) pyrometallurgical processing. By this is meant that the ultimate chemical step in making such cuprous material prior to using it as a grind charge here is, for example, effected by the heating of the copper metal and/or a copper compound such as a copper oxide or carbonate in an inert and/or a chemically reactive atmosphere (usually a reducing or an oxidizing one) or in the substantial absence of any atmosphere. One typical source of such cupreous material is the mill scale that forms on the surfaces of hot copper ingots that are exposed to air; another is from the air-oxidized surfaces of hot copper machining chips and cuttings; another is the controlled air oxidation of copper particles; still another is from the collection of vaporized copper and/or an oxide of copper. Even cupreous material that has been generated initially by a hydrometallurgical process (such as by precipitation from aqueous solution) can be considered as being from pyrometallurgical processing for the instant purposes if such material is further processed with heating, for example to reduce or to oxidize it with a gas for conditioning it for the instant process. The cupreous material for making the grind charge can be the product of a single pyrometallurgical process as, for example, the air oxidation of copper pieces, or it can be a blend of products from a plurality of sources.

The grind charge advantageously has been comminuted to fairly small size in a mill with a short retention time such as a hammermill using swing or fixed hammers. Other conventional pulverizing apparatus also can be used for such operation preparatory to the high energy milling. Thus, one can use a roller mill, an attrition mill, or a fluid energy mill.

Especially advantageous for the instant process is the careful selection of a grind charge of analysis as outlined herein, and this coupled with the fineness of grind made by the high energy comminution of such charge (to give adequate surface area and crystal lattice distortion to the catalyst product). Desirably such comminution is operated continuously, that is, with continuous feed to and take-off from the high energy milling (commminuting) apparatus. Batch milling can be used for this step if desired, however. Illustrative of a useful batch mill is the Sweco (the trademark of Sweco, Inc.) vibratory mill. A continuous high energy comminution apparatus preferred is a so-called "Palla mill", the product of Humboldt-Wedag of West Germany. A smaller laboratory size vibratory mill that is useful is the Megapac (a trademmark of Pilamec Ltd.) mill. Such mills generally are called "vibratory ball mills"—although the grinding media inside the shell(s) is often other than spherical in shape. Such media typically is made of a hard ceramic (such as alumina, zirconia, a steel (such as a stainless steel, a low alloy steel, a nickel steel), tungsten carbide, etc., all conventional grinding media. Such mill generally oscillates with a compound motion that is imparted to to the shell(s) by an eccentric driving mechanism.

Another high energy mill useful for the instant purpose is the "Szegvari mill" made by the Union Process Company. It is basically a stirred ball mill, and it even can be modified in accordance with the precepts of U.S. Pat. No. 3,927,837. In summary, the high energy comminution in the instant process is done by an apparatus that has solid grinding media in it, is driven with substantially more horsepower per unit weight of grinding medium than is a convention tumbling ball mill, and provides a prolonged residence time (actually an average residence time in a continuous operation) for the grind charge typically of at least about 10 minutes to an hour or even longer if necessary or desired.

In a matter of a half hour to an hour such mill can comminute the grind charge to size much smaller than 10 microns average size, usually 2–7 microns. If additional size reduction is needed, the output can be recycled for remilling.

In a preferred processing operation for making the catalyst the grind charge has particle size no coarser than 150 mesh, and the particulates thereof contain about 75–95% cuprous oxide, about 2–10% cupric oxide, and about 2–15% elemental copper.

In another useful processing operation for making the catalyst the grind charge has at least about 95% of its particles not substantially larger than 325 mesh and the particulates charged contain about 30–75% cuprous oxide, about 10–45% cupric oxide, and about 4–25% elemental copper. To obtain the particular stoichiometry of such charge it is often necessary to blend two or more powders of differing oxide and elemental copper contents.

The following example shows the process embodiment and the catalyst embodiment now preferred for efficiency and economy, but should not be construed as limiting the invention. In this specification all parts are parts by weight, all percentages are weight percentages, all temperatures are in degrees Celsius, and all mesh sizes are U.S. Standard Sieve sizes unless otherwise expressly noted; additionally, in this specification an average particle size means the mass median particle size as measured with the Microtrac (a trademark of Leeds & Northrup Company) particle size analyzer, and Specific Surface Area (SSA) is measured by the BET (Brunauer, Emmett, and Teller) method.

EXAMPLE 1

A hammermilled grind charge of air-oxidized copper pieces was furnished. Its particle size was all −150 mesh (with about 90% being −325 mesh). Its approximate analysis was:

| Ingredient | Wt. % | |
|---|---|---|
| $Cu_2O$ | 89.27 | |
| CuO | 5.35 | |
| $Cu°$ | 6.03 | |
| | | (total to here 100.65%) |
| Nitric Acid Insolubles | 0.05 | |
| Fe | 0.02 | |
| Sn | 0.015 | |
| Pb | 0.02 | |
| SSA, $m^2/gm.$ | 0.23 | (specific surface area) |

The grind charge was fed continuously at a rate of 270 kilograms per hour into a Model 35 U Palla mill (steel shot as the grinding media) and withdrawn continuously therefrom. Estimated average milling time was a little less than about ½ hour.

The output from the mill was a high cuprous oxide catalyst for the reaction of methyl chloride with silicon to produce dimethyldichlorosilane. Such output had the following analysis:

| Ingredient | Wt. % | |
|---|---|---|
| $Cu_2O$ | 84.06 | |
| CuO | 10.16 | |
| $Cu°$ | 6.89 | |
| | | (total to here 101.1%) |
| $HNO_3$ Insolubles | 0.01 | |
| Fe | 0.04 | |
| Sn | 0.015 | |
| Pb | 0.03 | |
| SSA, $m^2/gm.$ | 1.34 | (specific surface area) |
| Particle size, microns | 5.75 | (mass median diameter) |

The output particles had substantial lattice distortion and could have had more (and more surface area) if reprocessed in the Palla mill.

EXAMPLE 2

Alloy particles containing 0.07% aluminum and 0.12% tin alloyed with copper (and containing less than about 0.1% other material) were air-oxidized at elevated temperature to a copper oxide-rich condition, then pulverized to make a particulate grind charge (−150 mesh) for high energy comminution.

The grind charge was batch-milled for about 6 hours in a "Megapac" mill to make a catalyst useful in the reaction of methyl chloride with silicon to produce dimethyldichlorosilane. Such catalyst exhibited crystal lattice distortion. In addition to aluminum and tin from the alloy, the catalyst had the following analysis:

| Ingredient | Wt. % | |
|---|---|---|
| $Cu°$ | 16.8 | |
| $Cu_2O$ | 39.2 | |
| CuO | 44 | |
| Nitric Acid Insolubles | 0.06 | |
| Fe | 0.02 | |
| Pb | 0.01 | |
| SSA, $m^2/gm.$ | 2.4 | (specific surface area) |

-continued

| Ingredient | Wt. % | |
| --- | --- | --- |
| Particle Size, microns | 3.4 | (mass median diameter) |

EXAMPLE 3

Alloy particles containing 0.75% iron, 0.12% tin, and 0.25% aluminum alloyed with copper (and containing less than about 0.2% other material) was air-oxidized at elevated temperature to a copper oxide-rich condition, then pulverized to make a grind charge (−150 mesh) for high energy comminution.

This grind charge was comminuted essentially like that of Example 2 to make a catalyst useful in the reaction of methyl chloride with silicon to produce dimethyldichlorosilane. Such catalyst exhibited crystal lattice distortion. In addition to iron, tin, and aluminum from the alloy, the catalyst had the following analysis:

| Ingredient | Wt. % | |
| --- | --- | --- |
| Cu° | 21.3 | |
| $Cu_2O$ | 34.5 | |
| CuO | 44 | |
| Nitric Acid Insolubles | 0.11 | |
| Pb | 0.01 | |
| SSA, $m^2$/gm. | 2.2 | (specific surface area) |
| Particle Size, microns | 3.5 | (mass median diameter) |

What is claimed is:

1. A process for producing catalyst from cupreous particulates containing a major proportion of cuprous and cupric oxides and a minor proportion of elemental copper which is characterized by:
   providing a grind charge of said particulates having average particle size above 15 microns,
   said charge containing zero to about 10% of promoter-providing material selected from the elements aluminum, zinc and iron, the oxides of aluminum, zinc and iron, the chlorides of aluminum, zinc, copper and iron, silica, aluminosilicates, or below 0.05% antimony promoter; and
   subjecting said charge to high energy comminution until the average particle size of the resulting grind is no larger than 15 microns.

2. The process of claim 1 wherein said cupreous particulates contain about 75-95% cuprous oxide, about 2-10% cupric oxide, and about 2-15% elemental copper, and said grind charge has particle size no coarser than about 80 mesh.

3. The process of claim 1 wherein said cupreous particulates contain about 30-75% cuprous oxide, about 10-45% cupric oxide, and about 4-25% elemental copper, and said grind charge has at least about 95% of its particles not substantially larger than about 325 mesh.

4. The process of claim 1 wherein at least the major proportion of said cupreous particulates for the grind charge are the products of pyrometallurgical processing.

5. The process of claim 4 wherein said cupreous particulates consist essentially of oxidized elemental copper that has been alloyed with promoter-providing material.

6. Particulate, high cuprous oxide catalyst for alkyl or aryl halosilane production, said catalyst consisting essentially of about 75-95% cuprous oxide, about 2-10% cupric oxide, about 2-15% elemental copper, and zero to about 10% promoter selected from the elements aluminum, zinc and iron, the oxides of aluminum, zinc and iron, the chlorides of aluminum, zinc, copper and iron, silica, aluminosilicates, or below 0.05% antimony promoter and having surface area of about 1-8 square meters per gram, average particle size no larger than 15 microns, and exhibiting crystal lattice distortion.

7. The catalyst of claim 6 whose particulates contain promoter derived from the oxidation of an alloy of copper with promoter-providing material.

8. Particulate medium content cuprous oxide catalyst for alkyl or aryl halosilane production, said catalyst consisting essentially of about 30-75% cuprous oxide, about 10-45% cupric oxide, about 4-25% elemental copper, and zero to about 10% promoter selected from the elements aluminum, zinc and iron, the oxides of aluminum, zinc and iron, the chlorides of aluminum, zinc, copper and iron, silica, aluminosilicates, or below 0.05% antimony promoter and having specific surface area of about 2.5-8 square meters per gram, average particle size below 15 microns, and exhibiting crystal lattice distortion.

9. The catalyst of claim 8 whose particulates contain promoter derived from the oxidation of an alloy of copper with promoter-providing material.

* * * * *